United States Patent
Renimel et al.

(10) Patent No.: US 7,563,463 B2
(45) Date of Patent: Jul. 21, 2009

(54) **COSMETIC SLIMMING COMPOSITION CONTAINING AN EXTRACT OF BIOMASS OF THE ALGA *NEOCHLORIS OLEOABUNDANS***

(75) Inventors: Isabelle Renimel, Trainou (FR); Cécile Lamy, Saint Jean de Braye (FR); Delphine Dupont, Dourdan (FR); Sylvie Darnault, Orleans (FR)

(73) Assignee: LVMH Recherche, Saint Jean de Braye (FR)

( * ) Notice: Subject to any disclaimer, the term of this patent is extended or adjusted under 35 U.S.C. 154(b) by 0 days.

(21) Appl. No.: 11/818,125

(22) Filed: Jun. 13, 2007

(65) Prior Publication Data

US 2008/0038290 A1  Feb. 14, 2008

(30) Foreign Application Priority Data

Aug. 11, 2006  (FR) .................................. 06 53364

(51) Int. Cl.
- *A01N 65/00* (2006.01)
- *A01N 25/00* (2006.01)
- *A61K 36/00* (2006.01)
- *A61K 8/02* (2006.01)
- *A61K 47/00* (2006.01)

(52) U.S. Cl. .................. 424/725; 424/401; 514/783

(58) Field of Classification Search ................ None
See application file for complete search history.

(56) References Cited

FOREIGN PATENT DOCUMENTS

| | | |
|---|---|---|
| EP | 1 302 189 A1 | 4/2003 |
| FR | 2 657 012 | 7/1991 |
| FR | 2 785 910 | 5/2000 |
| FR | 2 873 038 | 1/2006 |
| FR | 2 873 038 A1 | 1/2006 |
| WO | 2006/122299 A2 | 11/2006 |

OTHER PUBLICATIONS (Tornabene et al, Lipid composition of the nitrogen starved green alga *Neochloris oleoabundans*, Enzyme Microb. Technol/. 5: 435-440, 1983).*
Tornabene, Lipid composition of the nitrogen starved green alga *Neochloris oleoabundans*, Enzyme Microb. Technol., 1983, 5: 435-440.*
Bligh et al., A rapid method of total lipid extraction and purification, Canadian Journal of Biochemistry and Physiology, 37: 911-917, 1959.*
Lien et al., Microalgal production of oils and lipids, Energy from biomass and wastes (1983), 7th, 1107-22.*
French Search Report dated Mar. 22, 2007.
Humeau, et al., "Biodiversity of Microalgae: Beauty Care Applications" Jun. 30, 2004. XP001204854.
Combined Search and Examination Report issued by UK Intellectual Property Office Aug. 31, 2007.

* cited by examiner

*Primary Examiner*—Michele Flood
*Assistant Examiner*—Qiuwen Mi
(74) *Attorney, Agent, or Firm*—Hamre, Schumann, Mueller & Larson, P.C.

(57) ABSTRACT

A cosmetic composition comprising, as active agent, an extract of biomass of the alga *Neochloris oleoabundans*, the active agent being incorporated in a cosmetically acceptable vehicle compatible with topical application. This extract is advantageously an alcoholic or aqueous-alcoholic extract, called the first extract obtained by treating the biomass with a first alcoholic or aqueous-alcoholic solvent, and/or at least one fraction of the first extract, obtained by fractionating the first extract.

13 Claims, No Drawings

COSMETIC SLIMMING COMPOSITION CONTAINING AN EXTRACT OF BIOMASS OF THE ALGA *NEOCHLORIS OLEOABUNDANS*

The invention relates to the use of an extract of biomass of the alga *Neochloris oleoabundans* in the field of cosmetics, and more particularly as a slimming agent in a cosmetic composition.

Numerous uses of microorganisms in cosmetic or dermatological compositions are known.

The taxonomic information concerning the alga *Neochloris oleoabundans* is given below:
  Division: Chlorophyta
  Class: Chlorophyceae
  Order: Chlorococcales
  Family: Chlorococcaceae
  Genus: *Neochloris*
  Species: *oleoabundans*

This alga is a microalga forming part of the numerous microorganisms and algae cited in international patent application WO 2006/008401, which describes a process for the preparation of a clarified culture medium of at least one photosynthetic marine and/or freshwater microorganism, and the use of these clarified culture media, especially in the field of cosmetics.

Said document expresses no interest in the use of the biomass itself, but only in the use of the clarified culture medium.

The literature so far contains no indications of the use of extracts of biomass of the alga *Neochloris oleoabundans* as an active agent of a cosmetic composition.

The experiments carried out by the inventors of the present invention on different extracts of biomass of this alga showed that they were of very particular value in the field of cosmetics, especially as a slimming agent.

More precisely, it was apparent to the inventors of the present invention that the extracts of biomass of the alga *Neochloris oleoabundans* obtained by means of polar and/or apolar solvents exhibited very valuable slimming properties when they were applied topically to the skin, particularly in cosmetic compositions.

It was apparent, however, that certain extracts of this alga proved particularly valuable for their slimming properties. This is the case of extracts obtained by means of polar solvents, particularly alcoholic or aqueous-alcoholic extracts. Furthermore, it was also apparent that these extracts obtained by means of polar solvents, particularly alcoholic or aqueous-alcoholic extracts, could subsequently be subjected to various fractionation operations that made it possible in particular to obtain novel extracts, said extracts themselves also exhibiting valuable slimming properties while at the same time having organoleptic properties or a coloration that are distinctly improved compared with the first alcoholic or aqueous-alcoholic extracts.

Thus, according to a first feature, the invention relates to a cosmetic composition comprising an extract of biomass of the alga *Neochloris oleoabundans*.

According to a second feature, the invention relates to a process for the preparation of the extracts useful for carrying out the present invention.

According to a third feature, it relates to the application of these same extracts as a slimming agent in the field of cosmetics.

According to the essential characteristic of its first feature, the invention relates to a cosmetic composition comprising, as active agent, an extract of biomass of the alga *Neochloris oleoabundans*, said active agent being incorporated in a cosmetically acceptable vehicle compatible with topical application.

As explained earlier, the extracts of biomass of the alga *Neochloris oleoabundans* have valuable slimming properties when they are applied to the skin.

There are various culture conditions that produce the biomass used according to the invention. However, the alga *Neochloris oleoabundans* will preferably be cultivated in a culture medium based on seawater or a brackish water with a sodium chloride content of between 10 g/l and 30 g/l, preferably of between 16 g/l and 20 g/l, this medium also optionally containing nutrients that are conventionally used.

Particularly advantageously, the sodium chloride content will be 18 g/l.

The culture medium advantageously comprises brackish water, i.e. a mixture of seawater and fresh water.

The seawater used will preferably be taken from the English Channel along the northern coast of Brittany, particularly in the Roscoff region (Finistère, France).

As explained earlier, the extracts used to prepare the cosmetic compositions of the invention will advantageously be alcoholic or aqueous-alcoholic extracts or extracts resulting from a fractionation of the latter.

In the description which follows, first extract is understood as meaning the alcoholic or aqueous-alcoholic extract obtained by treating the biomass with a first alcoholic or aqueous-alcoholic solvent.

In one advantageous variant of the invention, this first extract, which has valuable slimming properties, is used as a slimming agent in the compositions of the invention.

In other variants, the active agent used in the cosmetic compositions of the invention is a fraction obtained by fractionating this first extract.

In yet another variant, a mixture of the first extract, as defined above, and at least one fraction of this first extract, obtained by fractionation thereof, may be used in the composition of the invention.

The first extract will advantageously be prepared using a first alcoholic or aqueous-alcoholic solvent in which the alcohol is selected from the group consisting of $C_1$ to $C_5$ monoalcohols, $C_2$ to $C_6$ glycols and mixtures thereof.

Methanol, ethanol and butylene glycol may be mentioned in particular as examples of these alcohols.

The composition of said first solvent can vary within very wide limits of water and alcohol. However, in the case of a mixture of ethanol and water, the respective proportions of these two constituents will be chosen in the range from 100% to 40% by volume of ethanol and 0% to 60% of water.

As explained above, the first extract obtained by extraction of the biomass with an alcoholic or aqueous-alcoholic solvent has particularly valuable slimming properties, making it a particularly valuable extract as an active agent in terms of the invention.

As also explained above, especially for the purpose of improving the organoleptic properties of the extract and/or reducing its coloration, the first extract may be subjected to various fractionation operations to give novel extracts with improved properties, particularly improved organoleptic properties and/or a reduced coloration.

In one advantageous variant of the invention, the first extract is subjected to a partition step by liquid-liquid extraction between a second aqueous or aqueous-alcoholic solvent and a third solvent that is immiscible with the second solvent and has a polarity of between 0 and 4.7, defined by its polarity coefficient P', which produces an aqueous-alcoholic phase comprising a first fraction of the first extract, called the second extract, and a phase consisting of the third solvent and comprising a second fraction of the first extract, called the third extract.

For the definition of the polarity coefficient P', reference may be made to the publication by L. R. SNYDER entitled "Classification of the solvent properties of common liquids" in Journal of Chromatography 92 (1974) 223-230.

For this fractionation step, the second solvent advantageously consists of a mixture of water and an alcohol selected from the group consisting of $C_1$ to $C_5$ monoalcohols and $C_2$ to $C_6$ glycols.

Methanol, ethanol, butylene glycol and mixtures thereof will be chosen as the preferred alcohol.

Those skilled in the art will understand that the proportions of water and alcohol depend on the nature of the alcohol, but also on that of the third solvent.

If the second solvent is aqueous-alcoholic and comprises ethanol, the latter is advantageously present in a proportion of at least 20% by volume.

The third solvent, which is immiscible with the second solvent and has a polarity P' of between 0 and 4.7, is advantageously selected from the group consisting of chloroform, ethyl acetate, diethyl ether and mixtures thereof.

As explained earlier, the second and/or third extract, as defined above, will advantageously be chosen as an extract constituting an active agent in terms of the invention.

The proportions of extract(s) comprised in the compositions of the invention can vary within very wide limits.

However, these proportions will advantageously be between 0.0003 and 2% by weight, based on the total weight of the composition, the percentage being expressed as dry extract(s).

These proportions are advantageously between 0.003 and 0.3% by weight.

Furthermore, in one particularly advantageous embodiment, even if the extract is not obtained by extraction with butylene glycol, it proves valuable to introduce it into the composition of the invention in the form of a solution in a mixture of water and butylene glycol and particularly in the form of a solution containing from 0.05 to 5% by weight and preferably from 0.1 to 1% by weight of dry extract, based on the weight of the water/butylene glycol mixture.

This will advantageously be done using a 50/50 by volume mixture of water and butylene glycol.

According to a second feature, the invention relates to a process for the preparation of an extract of Neochloris oleoabundans intended especially for the preparation of a composition as defined above. This process comprises at least one step for extraction of the biomass with a first alcoholic or aqueous-alcoholic solvent, as defined above, to give a first extract.

This process advantageously also comprises at least one step for fractionation of this first extract.

In one advantageous variant, this fractionation of the first extract consists of a step for partition of the first extract between a second aqueous-alcoholic solvent and a third solvent that is immiscible with the second solvent and has a polarity P' of between 0 and 4.7, said partition producing a second and a third extract respectively contained in each of the phases made up of the second and third solvents.

Finally, the process of the invention may comprise additional conventional steps for purification of the different extracts for the purpose of improving their organoleptic qualities or their coloration.

Examples of such steps which may be mentioned are steps for decolorization over activated charcoal, e.g. XCV charcoal, or filtration steps, e.g. with a filter cut-off of between 40 and 0.20 µm.

The invention further relates to the use of the extracts or mixtures of extracts as defined above, or as obtained by the process defined above, as a slimming agent in a cosmetic composition or for the manufacture of a cosmetic composition.

The results given in the Examples which follow clearly illustrate the lipolytic activity of the extracts according to the invention by monitoring the release of fatty acids in situ from skin explants.

Finally, according to a final feature, the invention relates to a method of cosmetic care of the human body in order to obtain a slimming effect. This method comprises the application of a composition as defined above to a part of the body in need thereof.

Such a method comprises selecting the part of the body that requires a slimming treatment, and applying a composition of the invention to this part of the body.

The Examples which follow illustrate the invention without implying a limitation.

EXAMPLES

I. Culture of the Alga *Neochloris Oleoabundans* and Recovery of the Biomass

The strain used originates from the UTEX algotheque (algae collection of the University of Texas in Austin) and has the reference UTEX 1185. This strain was isolated in Saudi Arabia.

In the context of the Example, the culture was effected in batch mode in a 20 $m^3$ tank filled with brackish water containing 18 g/l of salt, with the addition of a nutrient medium of the following composition:

$Na_2EDTA$: $4.36.10^{-3}$ g/l
$FeCl_3.6H_2O$: $1.58.10^{-3}$ g/l
$NaHCO_3$: $0.6.10^{-3}$ g/l
$MnCl_2.4H_2O$: $0.36.10^{-3}$ g/l
$CuSO_4.5H_2O$: $1.10^{-5}$ g/l
$ZnSO_4.7H_2O$: $2.2.10^{-5}$ g/l
$CoCl_2.6H_2O$: $1.10^{-5}$ g/l
$MgSO_4$: $4.95.10^{-2}$ g/l
$NaNO_3$: 0.17 g/l
$H_3BO_3$: $2.47.10^{-3}$ g/l
$NaHCO_3$: $4.23.10^{-3}$ g/l
$K_2HPO_4$: $3.475.10^{-2}$ g/l
$CaCl_2$: $2.94.10^{-2}$ g/l
Vitamin $B_1$: $1.10^{-4}$ g/l
Vitamin $B_{12}$: $5.10^{-7}$ g/l
Vitamin H: $5.10^{-7}$ g/l It is also possible to employ a semicontinuous mode. In the type of tank used, the culture reaches maturity after 12 to 15 days.

At the end of this period, either all or part of the algal suspension is withdrawn.

The biomass is then concentrated by centrifugation with an acceleration of 14000 g (1 g=9.18 $m/s^2$).

II. Preparation of Extracts According to the Invention

1. Preparation of Extracts from a First Extraction with Methanol a. 250 ml of methanol are added to 100 g of algal biomass containing 26% of dry extract in a 500 ml round-bottomed flask. The mixture is heated at 65° C. for 30 minutes under nitrogen. The whole is centrifuged at 400 rpm for 10 minutes. The liquid phase is separated from the solid residue and discarded. The filtration residue is then transferred to a 250 ml round-bottomed flask and re-extracted with 250 ml of methanol under the same conditions. This operation is repeated one final time. The three liquid phases are pooled and then evaporated to dryness on a rotary evaporator. The solids obtained are resolubilized in 100 ml of water and then frozen and lyophilized. This extract is ultimately in the form of a powder and is hereafter denoted as extract A.

a.1. Following the same preparatory scheme as that described in item a), the liquid phase, which is again collected, is evaporated to dryness on a rotary evaporator and then resolubilized, but this time with 200 ml of heptane. The whole is treated with ultrasound and then centrifuged for 30 minutes at 4000 rpm. The supernatant is recovered, evaporated to dryness on a rotary evaporator and then resolubilized by adding 100 ml of distilled water, frozen and then lyophilized to give an extract, which is hereafter denoted as A1.

a.2. Following the same extraction scheme as that described for the preparation of extract A in item 1.a), the filtration residue obtained by extraction with methanol is in this case resolubilized in 100 ml of chloroform, and 95 ml of water and 5 ml of methanol are added. A liquid-liquid partition is effected between the two phases. The organic phase is discarded and the aqueous phase is rewashed twice with 50 ml of chloroform and then it too is discarded for the preparation of the extract described in item a. 3) below. The organic phases are pooled and then evaporated to dryness on a rotary evaporator, resolubilized in 50 ml of water and lyophilized. The resulting extract is hereafter denoted as A2.

a.3. The aqueous phase as defined in item a. 2) is evaporated on a rotary evaporator, resolubilized in 50 ml of water and lyophilized to give an extract, which is hereafter denoted as A3.

2. Preparation of an Extract B by a First Aqueous-Ethanolic Extraction and Fractionation of this Extract a. Preparation of an Aqueous-Ethanolic Extract B 250 ml of an ethanol/water mixture (94/4 volume/volume, hereafter v/v) are added to 100 g of algal biomass containing 14.6% of dry extract in a 500 ml round-bottomed flask. The mixture is refluxed for 30 minutes. After cooling, the extract is centrifuged at 4000 rpm for 20 minutes and the centrifugation residue is then re-extracted a total of 3 times with 250 ml of aqueous-alcoholic solution.

The supernatants are subsequently pooled, filtered on a Büchner funnel using a 0.40 μm filter (GF/F, Whatman) and then evaporated to dryness on a rotary evaporator.

The resulting extract B is then dissolved in DMSO at a concentration of 5% (weight/volume, hereafter w/v) for the biological tests.

b. Fractionation of Extract B by Liquid-Liquid Partition to Prepare an Extract B1 and an Extract B2

2 g of the previous extract B are diluted in about 80 ml of an ethanol/water mixture (20/40, v/v) to give a 2.5% solution. 53 ml of ethyl acetate are added to form a two-phase system. The two phases are separated in order to recover the first organic phase. The aqueous phase is rewashed with 53 ml of ethyl acetate and this is repeated a total of 4 times. The 4 organic phases are pooled and then evaporated on a rotary evaporator to give an extract, which is hereafter called extract B1.

The aqueous phase is also dried on a rotary evaporator to give a dry extract, which is hereafter called extract B2.

Extract B1 is solubilized in DMSO at a concentration of 5% (w/v) and extract B2 is dissolved in water at a concentration of 5% (w/v) for the biological tests.

3. Preparation of an Extract C by a First Aqueous-Ethanolic Extraction 250 ml of an ethanol/water mixture (96/4, v/v) are added to 100 g of algal biomass containing 12% of dry extract in a 500 ml round-bottomed flask. The mixture is refluxed for 30 minutes. After cooling, the extract is centrifuged at 400 rpm for 20 minutes and the centrifugation residue is then re-extracted a total of 3 times with 250 ml of aqueous-alcoholic solution.

The supernatants are subsequently pooled, filtered on a Büchner funnel (GF/F filter, Whatman, 40 μm) and then evaporated to dryness on a rotary evaporator. The resulting dry extract is extract C. It is then dissolved in DMSO at a concentration of 5% (w/v) for the biological tests.

III. Assay of the Lipolytic Activity of the Extracts of the Invention

III 1. Principle of the Assay

The object is to evaluate the lipolytic activity of extracts of *Neochloris oleoabundans* according to the invention on explants of adipose tissues that are kept alive.

The different extracts are incorporated into the culture medium under the conditions described below.

After a contact time of 8 days, the activity is evaluated by assaying the fatty acids released into the culture medium.

III 2. Procedure

Explants:
Preparation of 9 explants of adipose tissues and keeping them alive in BEM (BIO-EC's Explants Medium)
Division of the explants into 3 batches of 3 explants:
a reference batch, in the presence of the culture medium
a batch treated with caffeine as a positive reference
a batch treated with an extract according to the invention Test Products:
Positive reference: The caffeine is used at a final concentration of 0.1% (1 mg/ml) in the survival medium, i.e. at a concentration ten times greater than that of the extracts according to the invention, the caffeine no longer having a lipolytic effect at a concentration of 0.01% (100 μg/ml).
Extract of Neochloris according to the invention: The extract is in the form of a dry powder which is solubilized in DMSO at a concentration of 50% and then diluted to 1/500 in the explant culture medium so as to be tested at a final concentration of 0.01% (100 μg/ml).

Application of the Extracts:
At D0 the explants are kept alive in 2 ml of culture medium in which the test extract is incorporated.
This treatment is repeated at D2, D4 and D6.

Samplings:
At D2, D4, D6 and D8 the culture medium is sampled. For each explant the media sampled at D2, D4, D6 and D8 are combined in the same tube and stored at −20° C. for assaying the fatty acids present in the medium.

Assay of the Free Fatty Acids Present in the Medium:
After extraction of the culture medium, the free fatty acids present therein are separated off and assayed by high performance thin layer chromatography.

III 3. Results
The viability and morphology of the adipocytes are monitored by histology. After being kept alive for 8 days, the reference and treated explants exhibit neither visible degradation nor cell necrosis.

The lipolytic activity is evaluated by determining the proportions of free fatty acids released into the culture medium.

The results obtained are given in the Tables below and correspond to the weights of fatty acids released into the culture medium during the eight days of treatment, expressed in μg.

a. Results Obtained with Extract B According to the Invention

Fatty Acids Released (weights in μg)

|  | Mean | Standard deviation |
| --- | --- | --- |
| Reference | 8.7 | 1.4 |
| Caffeine 0.1% | 46.9 | 6.7 |
| Extract B 0.01% | 16.2 | 2.8 | b. Results Obtained with Extract B1 (Ethyl Acetate Fraction)

Fatty Acids Released (weights in μg)

|  | Mean | Standard deviation |
| --- | --- | --- |
| Reference | 3.6 | 0.6 |
| Caffeine 0.1% | 12.9 | 1.8 |
| Extract B1 0.01% | 20.8 | 3.6 | c. Results Obtained with Extract B2 (Aqueous-Ethanolic Fraction)

Fatty Acids Released (weights in μg)

|  | Mean | Standard deviation |
| --- | --- | --- |
| Reference | 3.6 | 0.6 |
| Caffeine 0.1% | 12.9 | 1.8 |
| Extract B2 0.01% | 10.8 | 1.3 |

III 4. Conclusions

It is seen that all the test extracts according to the invention have a significant lipolytic activity inasmuch as a substantial amount of fatty acid is released into the medium. This lipolytic activity can even be considered as very significant, particularly that of extract B1, because at the 0.01% dose used for the extracts according to the invention, caffeine, a positive reference well known for its lipolytic activity, is no longer active.

IV. Formulation Examples

The topical cosmetic compositions described below are prepared in conventional manner from the following centesimal compositions, expressed by weight.

| Slimming gel | |
| --- | --- |
| Deionized water | 73.5% |
| Alcohol 96.2 vol % | 21 |
| AMPS polymer (Sepigel 305) | 3 |
| Preservative | 0.3 |
| Perfume concentrate | 0.1 |
| Extract of Neochloris oleoabundans (extract B1 at 3% in water/butylene glycol, 50/50) | 2 |
| Sodium hyaluronate (high molecular weight) | 0.1 |
| Slimming cream | |
| Glyceryl stearate + PEG-100 stearate | 6.0% |
| Hydrogenated polyisobutene | 3.0 |
| Squalane | 3.0 |
| Glyceryl caprylate/caprate triglycerides | 3.0 |
| Glycerol | 2.0 |
| Octyl methoxycinnamate | 2.0 |
| Cetylstearyl octanoate | 1.5 |
| Beeswax | 1.5 |
| Cetyl alcohol | 1.0 |
| Stearyl alcohol | 1.0 |
| Dimethicone | 1.0 |
| Xanthan gum | 0.2 |
| Extract of Neochloris oleoabundans (extract B2 at 3% in water/butylene glycol, 50/50) | 2 |
| Preservatives, perfume, colorants | 0.2 |
| Water | qsp |
| Fluid slimming emulsion | |
| Octyl palmitate | 7.0% |
| Glyceryl caprylate/caprate triglycerides | 3.0 |
| Octyl octanoate | 2.0 |
| Phenyl trimethicone | 2.0 |
| Glycerol | 2.0 |
| Stearic acid | 1.0 |
| Sorbitan | 1.0 |
| Cetyl alcohol | 0.5 |
| Stearyl alcohol | 0.5 |
| Extract C of Neochloris oleoabundans | 1 |
| Preservatives, perfume, colorants, neutralizer | 0.1 |
| Water | qsp |
| Slimming lotion | |
| Butylene glycol | 3% |
| EDTA | 0.1 |
| Solubilizer | 1 |
| Perfume concentrate | 0.1 |
| Alcohol | 5.2 |
| Extract A of Neochloris oleoabundans | 0.5 |
| Benzophenone-4 | 0.13 |
| Preservatives, perfume, colorants, neutralizer | 0.1 |
| Water | qsp |

The invention claimed is:

1. A cosmetic composition, comprising, as active agent, an ethanolic or aqueous-ethanolic extract of biomass of the alga *Neochloris oleoabundans*, said active agent being incorporated in a cosmetically acceptable vehicle compatible with topical application,
wherein the cosmetic composition is formulated as a gel, cream, emulsion or lotion suitable for topical application, and includes the extract in a concentration sufficient to obtain a slimming effect.

2. The composition according to claim 1, wherein the biomass is obtained by cultivation of the alga *Neochloris oleoabundans* in a culture medium comprising seawater or a brackish water with a sodium chloride content of between 10 g/l and 30 g/l, said medium also optionally comprising nutrients.

3. The composition according to claim 2, wherein the sodium chloride content of said culture medium is 18 g/l.

4. The composition according to claim 2, wherein the culture medium comprises a brackish water.

5. A cosmetic composition, comprising, as active agent, an ethanolic or aqueous-ethanolic extract or at least one fraction of said extract, of biomass of the alga *Neochloris oleoabundans*, said active agent being incorporated in a cosmetically acceptable vehicle compatible with topical application, wherein the cosmetic composition is formulated as a gel, cream, emulsion or lotion suitable for topical application, and includes the extract in an amount sufficient to obtain a slimming effect; wherein said extract is obtained by treating the biomass with an ethanol or ethanol-water solvent; and said at least one fraction is obtained by fractionating said extract.

6. The composition according to claim 5, wherein said first solvent comprises 40% to 100% by volume of ethyl alcohol and 0% to 60% by volume of water.

7. The composition according to claim 5, wherein said at least one fraction of said extract results from a partition step by liquid-liquid extraction of said extract between a second aqueous or aqueous-alcoholic solvent and a third solvent that is immiscible with the second solvent and has a polarity of between 0 and 4.7, defined by its polarity coefficient P', the partition step producing an aqueous-alcoholic phase comprising said fraction, and a phase including the third solvent and a second fraction of the extract.

8. The composition according to claim 7, wherein the second solvent is an aqueous-alcoholic solvent, the alcohol of the second solvent being selected from the group consisting of $C_1$-$C_5$ monoalcohols, $C_2$-$C_6$ glycols and mixtures thereof.

9. The composition according to claim 8, wherein said alcohol of the second solvent is methanol, ethanol or butylene glycol.

10. The composition according to claim 8, wherein said alcohol of the second solvent is ethanol and is present in said aqueous-alcoholic solvent in a proportion of at least 20% by volume.

11. The composition according to claim 7, wherein said third solvent is selected from the group consisting of chloroform, ethyl acetate, diethyl ether and mixtures thereof.

12. The composition according to claim 8, wherein the at least one fraction is the second fraction.

13. The composition according to claim 1, wherein the extract comprises 0.0003% to 2% by weight, expressed based on the weight of the composition.

\* \* \* \* \*